United States Patent

Holupka et al.

[11] Patent Number: 5,810,007
[45] Date of Patent: Sep. 22, 1998

[54] ULTRASOUND LOCALIZATION AND IMAGE FUSION FOR THE TREATMENT OF PROSTATE CANCER

[75] Inventors: Edward J. Holupka, Medway; Irving D. Kaplan, Newton, both of Mass.; Everette C. Burdette, Champaign, Ill.

[73] Assignee: Associates of the Joint Center for Radiation Therapy, Inc., Boston, Mass.

[21] Appl. No.: 507,199

[22] Filed: Jul. 26, 1995

[51] Int. Cl.$^6$ .................................................. A61B 8/00
[52] U.S. Cl. .................................. 128/660.03; 128/653.1
[58] Field of Search ................... 128/660.01, 660.03, 128/653.1; 364/413.21, 413.26; 378/82; 601/2–4; 607/97

[56] References Cited

U.S. PATENT DOCUMENTS

| | | | |
|---|---|---|---|
| 4,125,858 | 11/1978 | Hounsfield et al. | 358/82 |
| 4,586,512 | 5/1986 | Do-huu et al. | 128/660.03 |
| 5,178,148 | 1/1993 | La Coste et al. | 128/660.03 |
| 5,222,499 | 6/1993 | Allen et al. | 128/653.1 |
| 5,227,969 | 7/1993 | Waggener et al. | 364/413.26 |
| 5,234,004 | 8/1993 | Hascoet et al. | 128/660.03 X |
| 5,299,253 | 3/1994 | Wessels | 378/163 |
| 5,389,101 | 2/1995 | Heilbrun et al. | 128/653.1 X |
| 5,391,199 | 2/1995 | Ben-Haim | 607/122 |
| 5,411,026 | 5/1995 | Carol | 128/660.03 |
| 5,447,154 | 9/1995 | Cinquin et al. | 128/660.01 X |
| 5,531,227 | 7/1996 | Schneider | 128/653.1 |

Primary Examiner—Francis Jaworski
Attorney, Agent, or Firm—Foley & Lardner; Michael D. Rechtin

[57] ABSTRACT

A method and apparatus for localizing and treating a patient's prostate by radiation therapy. The system includes an ultrasound probe for generating an ultrasound image of the prostate with the probe having at least two fiducial end points as landmarks. In addition, the system includes a CT apparatus to generate X-ray simulator images of the anatomical region near the prostate and further includes a computer executing computer software to transform the ultrasound image to the simulator image enabling accurate localization of the prostate relative to proximate anatomical features enabling accurate radiation therapy to be carried out on the prostate.

23 Claims, 8 Drawing Sheets

ULTRASOUND LOCALIZATION AND IMAGE FUSION FOR THE TREATMENT OF PROSTATE CANCER

The present invention is concerned generally with a method and apparatus for performing therapeutic treatments of prostate cancer. More particularly, the invention is concerned with a method and apparatus for accurately determining the location of the prostate for carrying out precision radiation therapy treatment of the prostate. The method and apparatus involve a pre-therapy, or planning, phase in which the prostate position is determined by a transrectal ultrasound image, relative to proximate anatomical structures defined by diagnostic X-ray images. The resulting prostate coordinates are then transformed to the coordinate system of the radiation therapy field for use during the treatment phase.

Adenocarcinoma of the prostate is the most commonly diagnosed noncutaneous cancer in the male population of the United States. It is estimated currently that 200,000 new cases of prostate cancer will be diagnosed each year. Approximately 16% of these newly diagnosed cases will be locally advanced non-metastatic cancers or, more specifically, AJCC stage III-T3N0M0. Treatment of patients in this stage is problematic. Significantly low rates of local control of the disease have been reported using conventional doses of radiation delivered with external beam radiation therapy for clinically locally advanced disease. In addition a smaller but significant proportion of patients with earlier staged disease develop recurrence after radiotherapy. Treatment of prostate cancer is difficult because of the extreme proximal position of radiation sensitive tissues, such as the bladder and rectum, and is further complicated by prostate motion relative to the radiation field on a daily basis. To improve the treatment outcome, more aggressive radiation techniques utilizing highly conformal fields and higher doses is being investigated. However, such dose escalated, conformal treatments cannot effectively be delivered without significant toxicity to normal tissues unless the exact position of the prostate can be determined and its spatial repositioning is dramatically reduced.

In general performing treatment of prostate cancer using radiation therapy involves the patient undergoing a conventional computerized tomography ("CT") scan of the pelvis to determine the approximate size, shape and location of the prostate gland. The position of the prostate is important since it is the intended target of the radiation. The patient then undergoes a treatment simulation in which planar, diagnostic X-ray films are taken in the plane of each of the proposed radiation fields. These X-ray films define where the prostate (or target volume) and radiation sensitive structures, such as the rectum and bladder, lie with respect to the radiation output portal. The goal of therapy is to treat the prostate with the prescribed dose, while minimizing the dose to the radiation sensitive structures. However, the prostate gland does not appear on these diagnostic X-ray (simulator) films. Therefore, the position of the prostate must be inferred from the previously acquired CT images and the relative position of the bladder, rectum and bony landmarks taken with the patient positioned differently than when the simulation films are taken. Since the position of the prostate is partially inferred from the position of the bladder and rectum, it is extremely important to accurately delineate these structures on the simulator films. This is normally achieved by inserting a catheter and injecting an X-ray contrast agent. Once the approximate position of the bladder, rectum and bony structures have been determined, the approximate shape and position of the prostate is hand drawn on the simulator films, aided by the information available from the CT images. The position of the bladder and rectum is determined from images taken at the time of simulation. The shape and position of the prostate is however obtained from CT images taken at a different time and patient position, and consequently a margin of dimensional safety must be drawn around the prostate volume to account for the variation of patient setup, target motion, and the spatial approximations inherent in localizing the prostate from the CT images to the simulator images. This margin is intended to insure that the prostate gland is receiving the intended dose. In the effort to insure that the prostate is receiving the proper dose, portions of the nearby rectum and bladder will also receive high doses. The close presence of these healthy structures limit the dose to the prostate. These proximal structures will then dictate what dose the prostate will receive, instead of the biology of the cancer. As a consequence of this uncertainty in prostate location, it has been postulated that currently accepted prescription doses for the prostate are in fact not optimal doses for the control of the disease. Local recurrence rates for prostate cancer using standard radiation therapy are high, approximately 50%, for larger tumors.

In an attempt to minimize the dose to normal tissues, in another conventional methodology radiation fields which geometrically correspond to the target volume can be used. Such therapies are called conformal therapies. There have been reports on the use of conformal techniques in an attempt to escalate the dose to the prostate with external beam radiation, although these methods are not in general use. Careful dose escalation studies are underway at several institutions to determine the acute and late toxicities of increased dose, albeit reduced volume of rectum and bladder. It has been reported that in a multivariate analysis fewer grade II toxicity's were observed in patients treated with conformal therapy. Low rates of chronic rectal morbidity have also been reported with similar conformal approaches. Conformal therapy does however require exact delineation of the target volume. This can be accomplished if the prostate tumor volume is accurately visualized and if one gains precise control or knowledge of those variables which determine the margin around the tumor volume. Microscopic disease, dose limiting structures such as the anterior rectal wall and prostate motion are important variables for determining the target volume. In spite of the promise of conformal therapy, this methodology is still plagued by the problems of prostate motion and inaccurate spatial localization.

It is therefore an object of the invention to provide an improved method and apparatus for radiation therapy treatment for prostate disease.

It is another object of the invention to provide a novel method and apparatus for accurately identifying the prostate position in preparation for prostate radiation therapy.

It is a further object of the invention to provide an improved method and apparatus for establishing an ultrasound image of the prostate and correlating that image to radiation therapy simulator images.

It is also an object of the invention to provide a novel method and apparatus for real time superposition of an ultrasound image of the prostate onto another image, such as a simulator or radiation therapy image.

It is yet another object of the invention to provide an improved method and apparatus for establishing at least two landmark points characteristic of patient anatomy for accurately positioning the prostate relative to radiation therapy fields.

It is an additional object of the invention to provide a novel method and apparatus for establishing landmark points on ultrasound and X-ray images to allow precise localization of the prostate relative to a radiation therapy field.

It is still a further object of the invention to provide an improved method and apparatus for accurately positioning the prostate (or patient) for radiation therapy using a couch mount for a transrectal probe having ultrasound transducer elements.

It is yet another object of the invention to provide a novel method and apparatus employing an ultrasound probe to form a geometry specific scan field with the transducer arc end points establishing landmark end points on an image enabling a mapping transformation to a simulator image preparatory to accurate radiation therapy.

These and other object of the invention will be described in detail in the description provided hereinafter and taken in conjunction with the drawings described below.

DETAILED DESCRIPTION OF PREFERRED EMBODIMENTS

Figure 1:
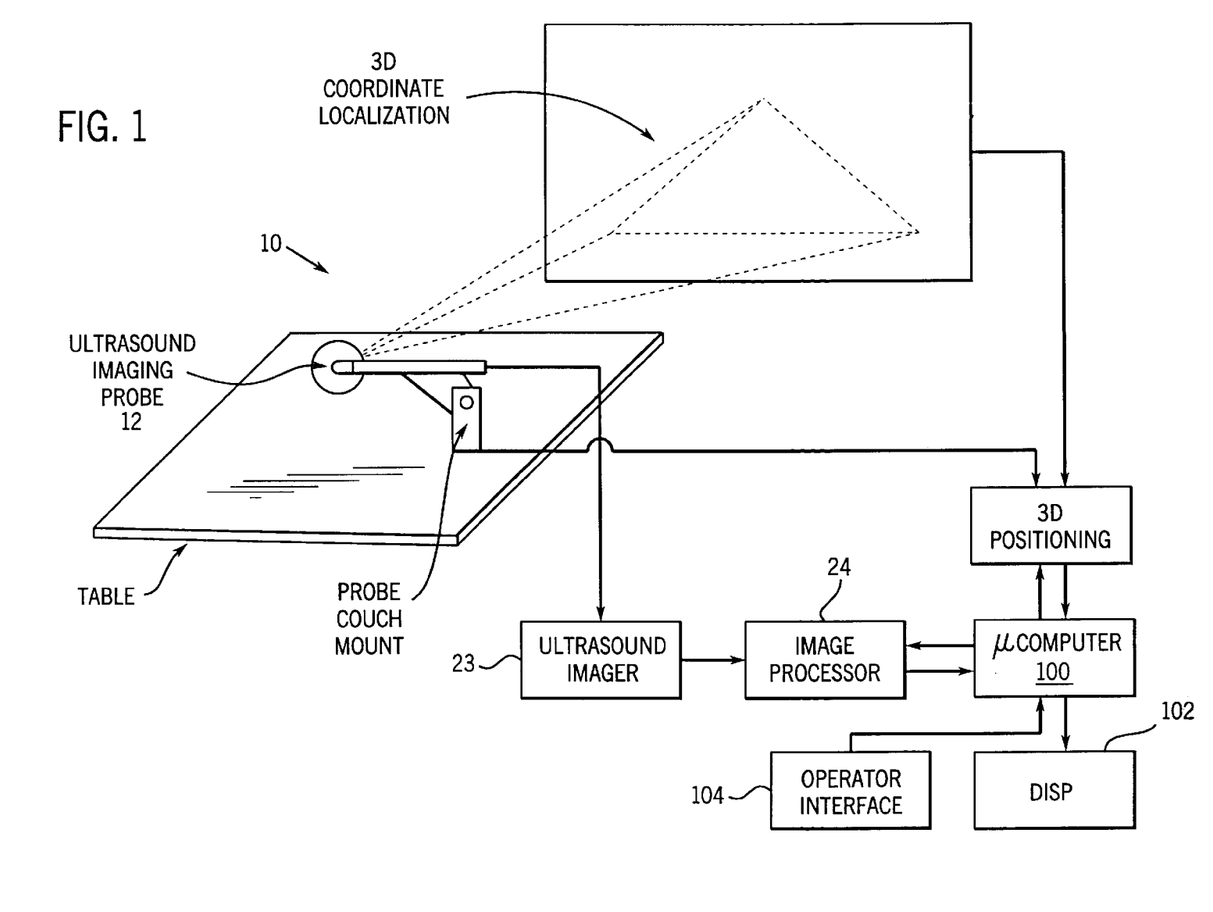
FIG. 1 illustrates a functional block diagram of an embodiment of the invention.
Figures 2, 9:
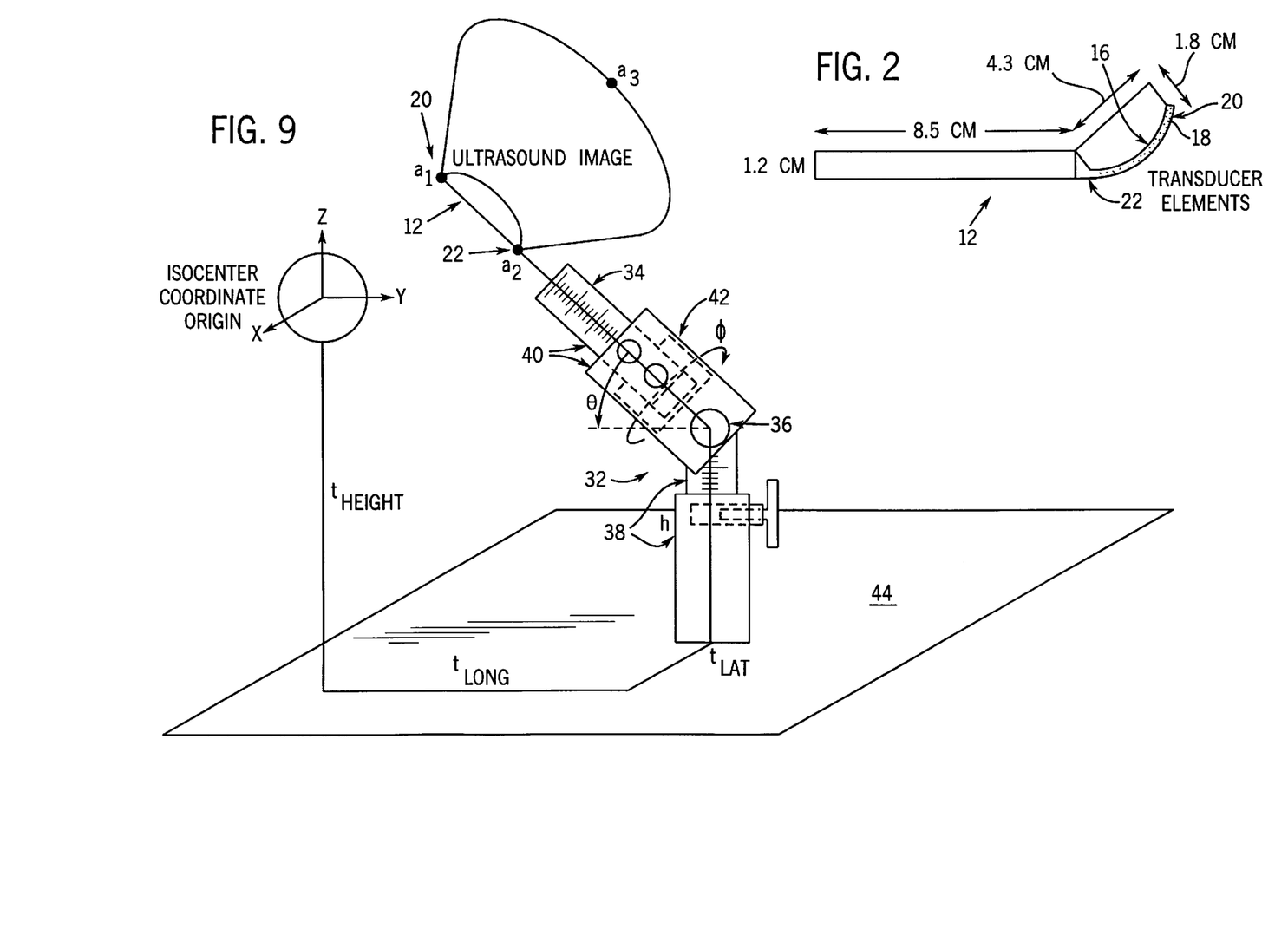
FIG. 2 illustrates a transrectal ultrasound probe used to generate an ultrasound image of the prostate anatomical region.
FIG. 9 shows the use of the couch mount of FIG. 8 for the transrectal probe of FIG. 2.

An illustration of the method and apparatus of the invention is shown in the components of the apparatus and images derived therefrom in the figures. In the functional block diagram of FIG. 1 is generally illustrated one embodiment of the invention. As shown in FIG. 2, in one preferred embodiment an ultrasound imaging system 10 (such as, a Dornier Urovision Ultrasound Imaging System) is utilized employing a transrectal ultrasound probe 12 (such as, a Dornier Model ER-S) operating at 5.6, 7.5, or 10 MHz. Any conventional ultrasound probe can be used, provided the probe construction permits definition of at least two landmark points, or fiducials. The probe 12 (best seen in FIGS. 1, 2, 8 and 9) includes a number of active transducer elements, such as ninety-six in the Dornier ER-S, with a display depth of 13.5 cm. Display depth is a function of frequency.

Figure 3:
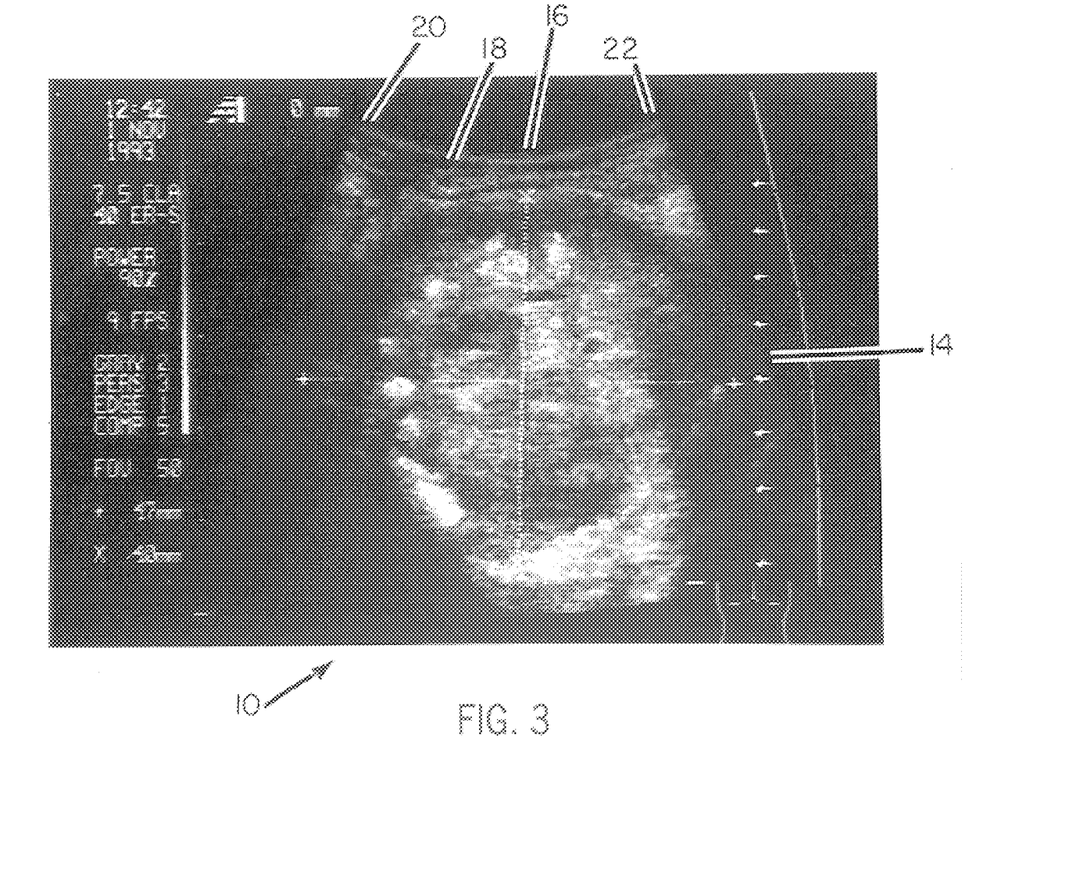
FIG. 3 illustrates an ultrasound image of the prostate region taken by the ultrasound probe shown in FIG. 2.
Figure 4:
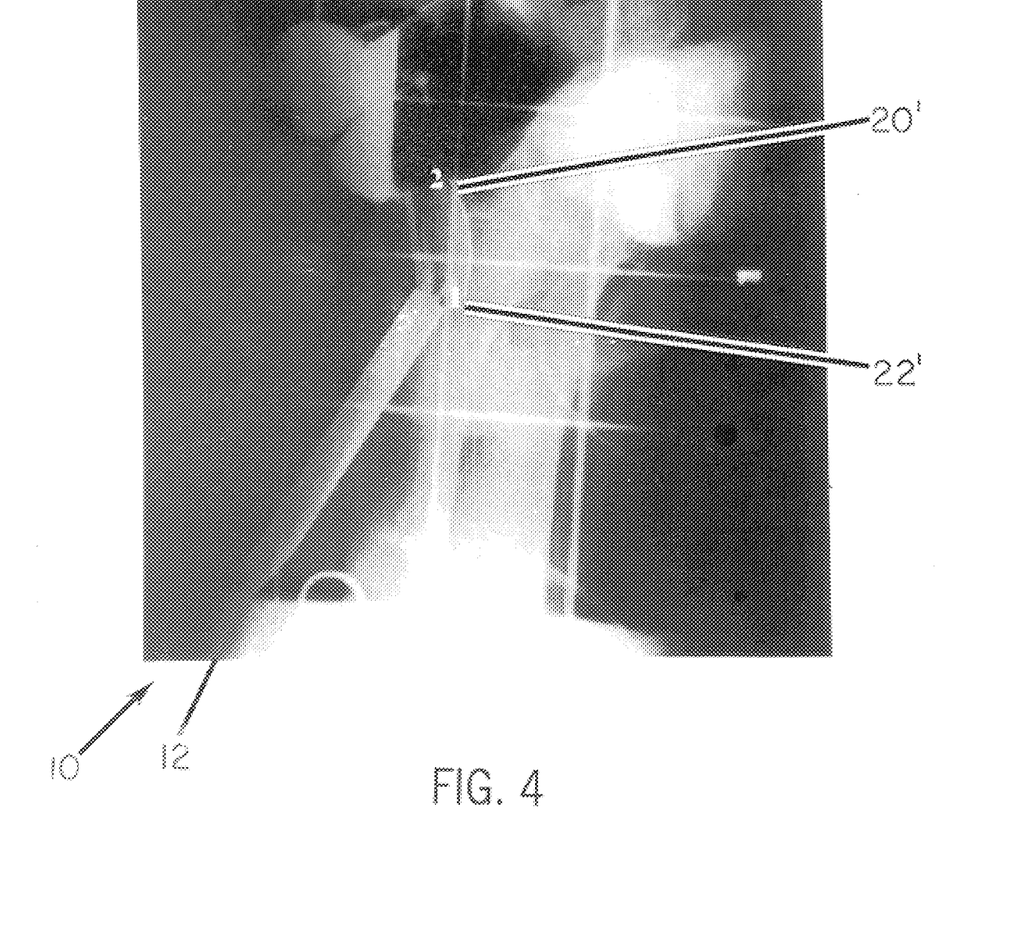
FIG. 4 illustrates a lateral simulator image displaying the location of the transrectal probe of FIG. 2.

In order to precisely localize the position of the prostate for radiation therapy, the diagnostic ultrasound image is fused, or correlated, with the simulator X-ray image by using a matching technique employing at least two points. This methodology requires the unambiguous identification of two fiducial points on each image (the ultrasound and X-ray images). The transrectal ultrasound probe 12 in FIGS. 1 and 2 utilizes a curved phased array methodology for obtaining a fan shaped image 14 (see FIG. 3). Arc 16 at the top of the ultrasound image in FIG. 3 directly corresponds to the spatial position of a transducer array 18 inside the head of the probe 12. This can be applied to planar as well as curved arrays. In the typical transrectal ultrasound image of the prostate in FIG. 3, the end points (also recited herein as "fiducials") of the transducer arc are labeled "20" and "22" in the image. FIG. 4 displays the lateral simulator film with the transrectal ultrasound probe 12 in place. The transducer array 18 of the probe 12 is visible in both the ultrasound and simulator images (FIGS. 1, 3 and 4, respectively). The ends of the transducer array 18 which correspond to the points on the ultrasound image are likewise labeled "20" and "22." By selectively enlarging sections of images, the points which correspond to the fiducial landmarks (the end points 20 and 22) can be determined to within a single display pixel.

Once the fiducials have been identified in the image, a spatial transformation which maps the ultrasound image to the simulator image is determined. As shown in FIG. 1, the electronic data from the probe 12 is output to an ultrasound imager 23 for processing through imaging processor 24 to computer 100 which executes selected computer software (to be described hereinafter and/or set forth in Appendix A). The transformation consists of a two-dimensional rotation, translation and a global isotropic scaling of the appropriate data using computer software. This leads to a four parameter transformation, $$\begin{pmatrix} x_{si} \\ y_{si} \end{pmatrix} = \begin{pmatrix} m_{xx} & m_{xy} \\ -m_{xy} & m_{xx} \end{pmatrix} \begin{pmatrix} x_{us} \\ y_{us} \end{pmatrix} + \begin{pmatrix} t_x \\ t_y \end{pmatrix} = \\ \lambda \begin{pmatrix} \cos\theta & \sin\theta \\ -\sin\theta & \cos\theta \end{pmatrix} \begin{pmatrix} x_{us} \\ y_{us} \end{pmatrix} + \begin{pmatrix} t_x \\ t_y \end{pmatrix} \quad (1)$$

where the four parameters are the translations, $t_x$ and $t_y$, the rotation angle, $\theta$, and the global scaling, $\lambda_o$. The vectors $\vec{r}_{us}$ and $\vec{r}_{is}$ represent the coordinates vector of any point in the ultrasound and simulator images respectively. If the two fiducial end points 20 and 22 on the ultrasound image are $\vec{r}_{us}(1)$ and $\vec{r}_{us}(2)$, and the two fiducial end points 20' and 22' on the simulator film are $\vec{r}_{si}(1)$ and $\vec{r}_{si}(2)$, then the matrix, $\underline{M}$ and translation $\vec{t}$, which maps the ultrasound image to the simulator image is given by the solution to the linear system of equations given by, $$\begin{pmatrix} x_{us}^{(1)} & y_{us}^{(1)} & 1 & 0 \\ -y_{us}^{(1)} & x_{us}^{(1)} & 0 & 1 \\ x_{us}^{(2)} & y_{us}^{(2)} & 1 & 0 \\ -y_{us}^{(2)} & x_{us}^{(2)} & 0 & 1 \end{pmatrix} \begin{pmatrix} m_{xx} \\ m_{xy} \\ t_x \\ t_y \end{pmatrix} = \begin{pmatrix} x_{us}^{(1)} \\ y_{us}^{(1)} \\ x_{us}^{(2)} \\ y_{us}^{(2)} \end{pmatrix} \quad (2)$$

Figure 5:
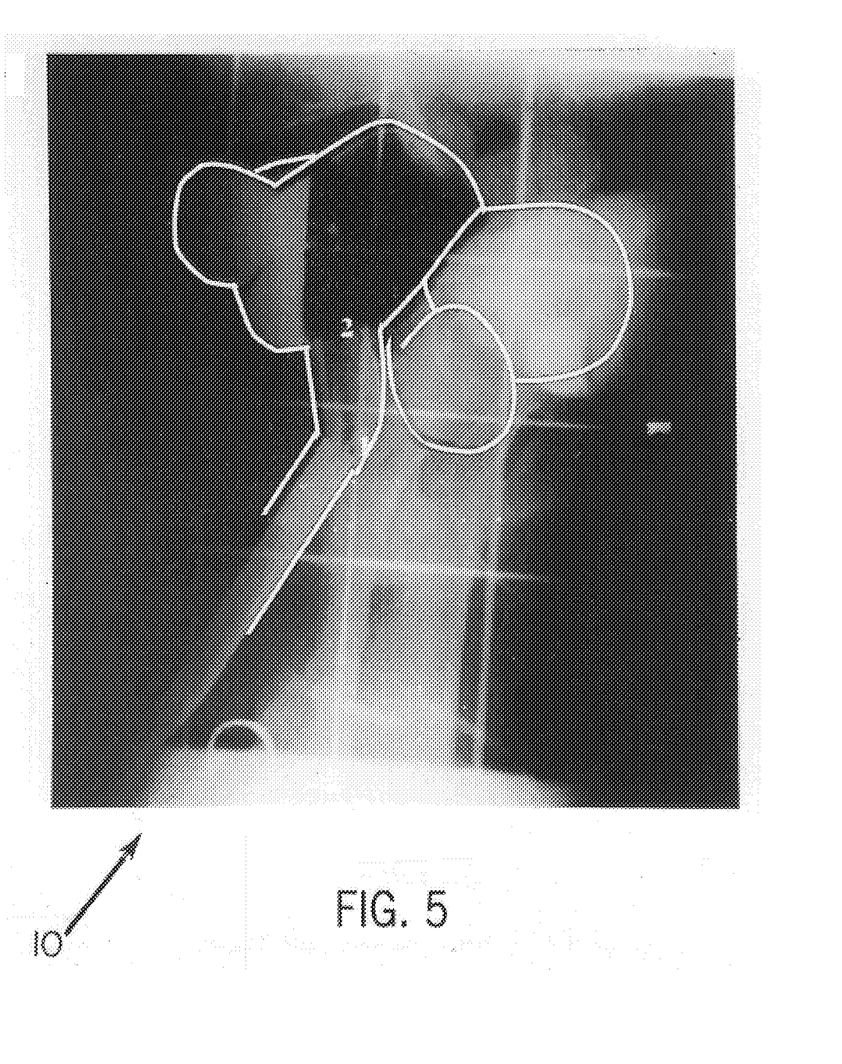
FIG. 5 illustrates a fusion image displaying the spatial mapping of the ultrasound image to the simulator image.

Once the solution for $M_{xx}$, $M_{xy}$, $t_x$ and $t_y$ are known, every point in the ultrasound image can be mapped to the simulator image using equation (2). FIG. 5 displays the result of transforming the ultrasound image to the simulator image. This will be referred to as the fusion image. FIG. 3 displays the ultrasound image data along with other useful diagnostic information supplied by the imaging system 10. However, only the ultrasound image data is transformed so that the details of the underlying radiographic image are not obscured.

The accuracy of the rotational and translational component of the transformation is determined by the accuracy of localizing the two end points 20 and 22 on the ultrasound image and the end points 20' and 22' on the radiographic images. The end points 20 and 22 corresponding to the ultrasound image can be determined automatically since for a given setting of the field of view (FOV) of the ultrasound imaging system 10, the position of the end points 20 and 22 of the transducer array 18 always appear at the same points, or display pixels, in the digitized image. The automatic determination of the fiducials (the end points 20' and 22') on the simulator image is more difficult since the probe 12 does not always appear exactly in the same position on the radiographic image as in the ultrasound image. To achieve automatically the locations of these end points, a conventional Hough transform can be used to effectively and automatically locate the two points 20' and 22' on the simulator image, provided the outline of the transducer array 18 is used as the Hough transform template. There will be two modes, manual and automatic, for the determination of the fiducials (end points 20' and 22'). For the manual mode, the image can be enlarged (zoomed) and the end points of the transducer array 18 can be determined to within a pixel (the smallest image point). Therefore, the accuracy of the spatial position of the fusion is determined by the pixel size (typically about 0.275 mm) for the simulator image. The limit of the accuracy for automatic fiducial detection on the radiographic image using a Hough transform is also determined by the pixel size.

Figure 6:
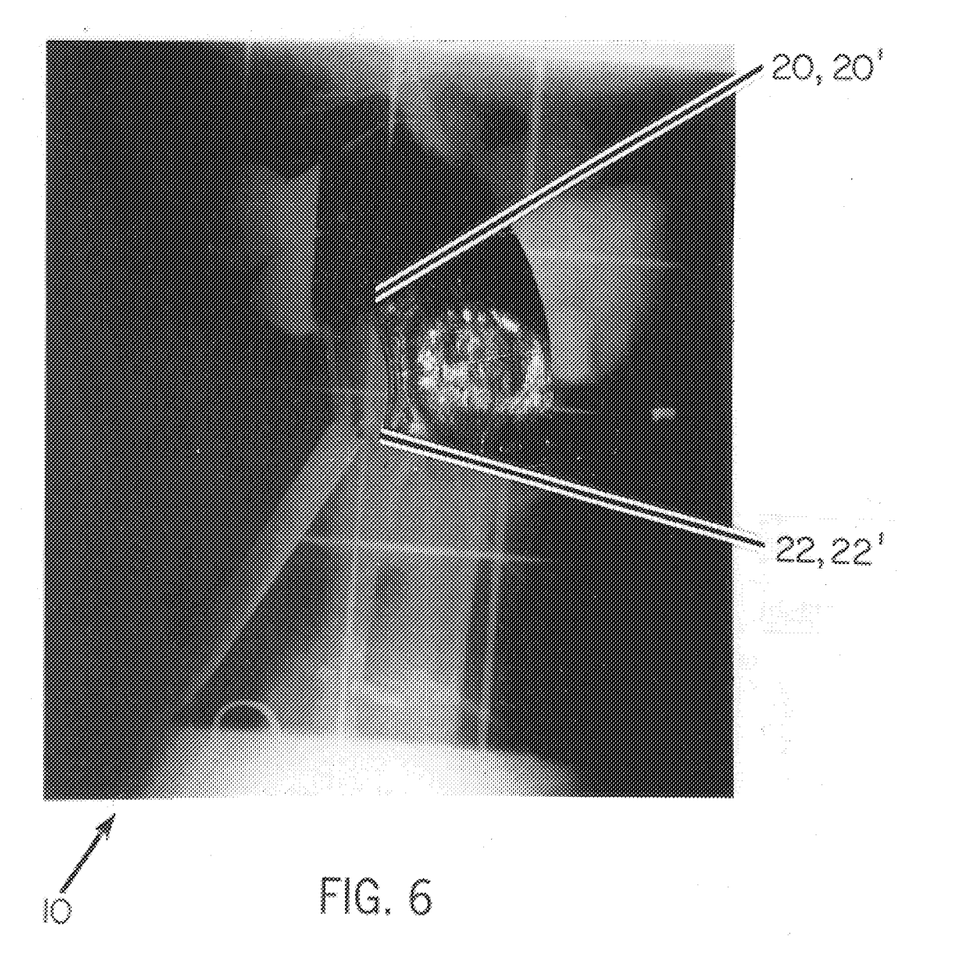
FIG. 6 illustrates selected anatomical regions of interest in the vicinity of the prostate treatment area.

After the ultrasound image is transformed to the simulator image, anatomical volumes of interest can be manually contoured on the fusion image. For example, FIG. 6 displays the fusion image where the prostate, bladder, and rectal volumes are contoured and color washed over the underlying image. A "color wash" is a graphics technique where a color image is "washed" over a gray scale image in such a way that the underlying gray scale image is still visible. If the pixels of the color image and the gray scale image are represented in Hue-Saturation-Value (HSV) space, then the color washed image is obtained by setting the value to the value of the gray scale image and setting the hue to the hue of the color image. The saturation is set to unity. The resulting image looks like the original gray scale image but with transparent colors of the color image.

Figure 7:
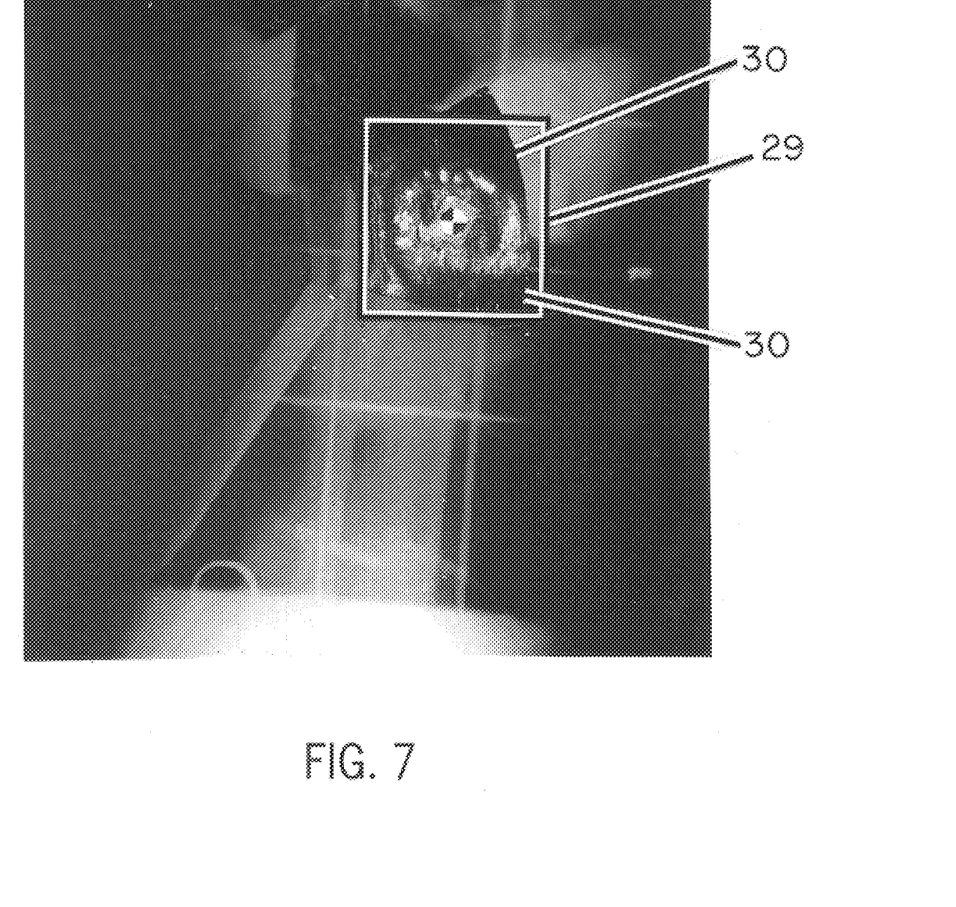
FIG. 7 illustrates selected anatomical regions of interest and the radiation portal disposed nearby.

The color washed representation of the volumes allow for the complete delineation of the volumes, while still allowing the structure of the underlying image, whether it be the ultrasound, treatment, or simulator image, to show through. In addition, the proposed radiation treatment field isocenter, width and height can be specified. FIG. 7 displays the fusion image with the contoured volumes of interest and proposed radiation field 29 superimposed. In addition to the field outline, a block 30, which appear as a white edge outlined square region, in the figure has also been drawn. The block 30 has been chosen to minimize rectal wall and bladder involvement in the field while ensuring that the tumor volume with a 0.5 to 0.75 centimeter margin receives 100% of the dose. Once the field 29 and the blocks 30 have been drawn, the percent area of prostate, bladder and rectum which is inside the radiation portal is automatically calculated and reported on the top of the fusion image. The area of the resultant radiation portal is also calculated and displayed. This quantitative information is available at the time of the simulation or treatment and may prove to be clinically valuable when assessing efficacy and morbidity.

To aid in the development of an accurate treatment plan, options are available through use of the computer 100 (see FIG. 1) to implement ultrasound fusion software (see attached Appendix A). The computer 100 interacts with the data from the probe 12 to produce the fusion image on a display 102. A user can interact by interface 104 with the imaging system 10 to carry out the functionalities described herein.

There are three basic modes of utilization: (1) the ultrasound mode, (2) the simulator mode, and (3) the fusion mode. All modes have the option of reading in new patient data, saving the present set of patient data, or restoring an old, previously saved set of patient data. All modes also have image enhancement functions such as windowing and leveling the image, edge detection, and enlargement or reduction of the image. Treatment planning to define the radiation field size 29, radiation blocks 30 and isocenter are available to each mode and include the ability to select and draw contours, activate a color wash of the contours and blocks, delete, add or delete points from a contour or block, measure absolute distance between points in the image specified by the mouse, and finally to fuse the images once all the point fiducials have been selected.

There are additional functions of the computer software which are specific to each basic mode. In the ultrasound mode, there exist options to flip the image about the vertical axis, manual or automatic specification of the end point fiducials used in the fusion algorithm, and automatic or manual cropping of the ultrasound image. Automatic cropping will crop the image using a special mask which will include only ultrasound image data for a specific mode of the imaging system 10. The simulator mode has the options for manual or automatic specification of the end point fiducials used in the fusion algorithm. The automatic definition of the end points fiducials for the simulator image is based on a Hough transform using the probe outline as a template. Once the contours have been specified, the computer software automatically calculates the area of the contour in square centimeters. Once the radiation field and the blocks 30 have been defined, the computer software can be used to determine the area of the contours which are directly involved in the radiation field. The size of the radiation field is also directly adjustable.

The data necessary to carry out therapy on a new patient include digitized ultrasound image and a digitized simulator image. The file format of these images is comprised of a header and string. The header contains patient information (name, age, etc.) followed by the image information (dimensions, etc.). This header is followed by a string of bytes which comprise the total image. Image compression is an option which can be selected by the user at the time the file is saved or restored. Once a patient file has been saved, a new file is created which contains the details of the contours, blocks, radiation field, fiducials, and image information (flipped status, cropped status, etc.).

Figures 8A, 8B:
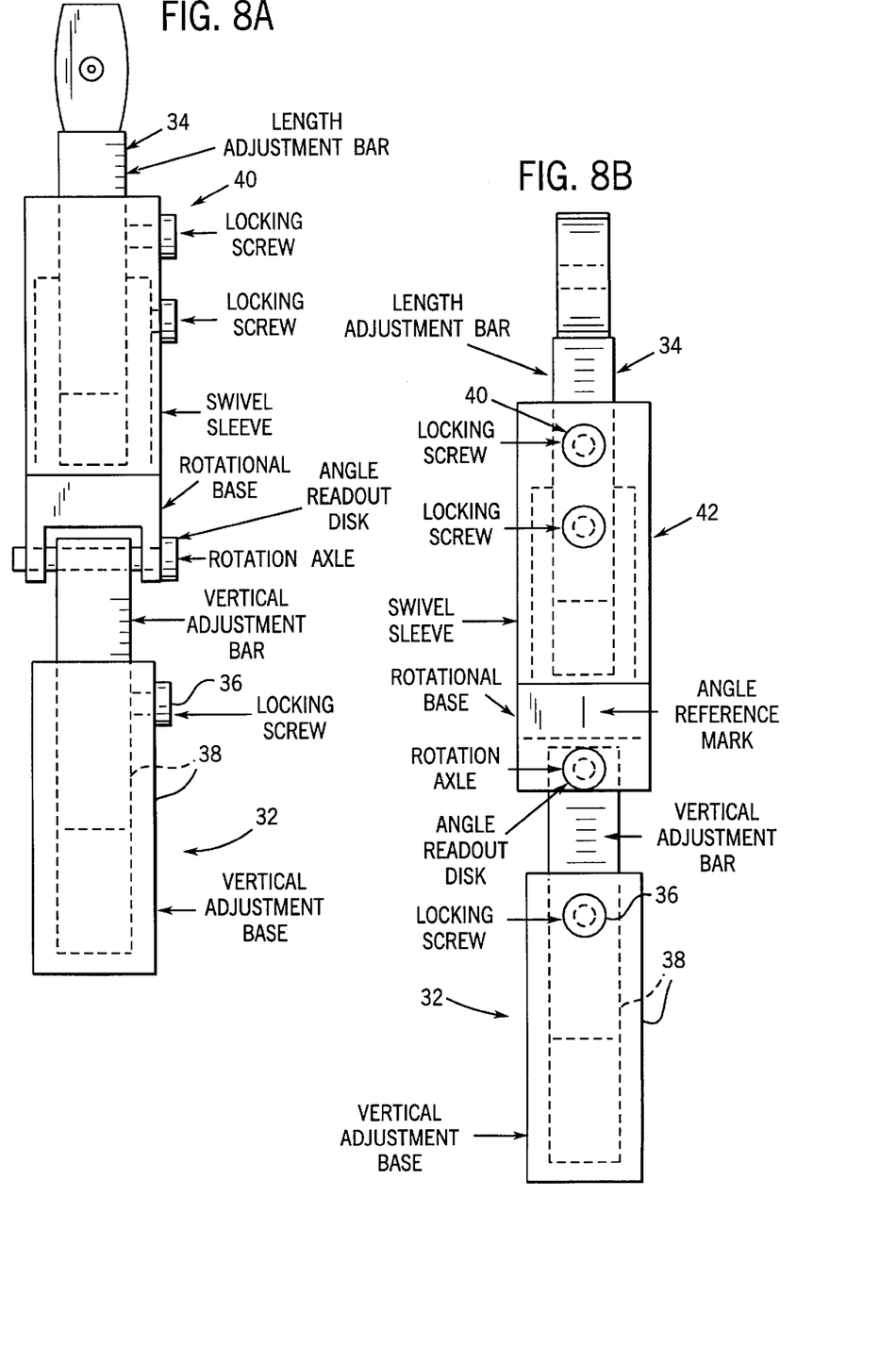
FIG. 8A is side view of a couch mount and FIG. 8B is a front view of the couch mount.

As shown in FIGS. 8 and 9, the couch mount 32 functions to accurately and reproducibly position the ultrasound probe 12 relative to the radiation field isocenter. This results in the localization of the ultrasound imaging plane relative to the radiation field isocenter or beam delivery system. In addition, this particular design is intended to be simple, which aids in the positioning and insertion of the probe 12 into the patient. The isocenter is chosen to be the coordinate origin. The couch mount 32 consists of six basic parts: (1) probe holder 34, (2) a first mechanism 36 for the angular positioning of the probe, (3) a second mechanism 38 for the vertical positioning of the probe 12, (4) a third locking screw mechanism 40 for the fixing of position of the probe 12 along the holder 34, (5) a machine 42 for rotational positioning of the probe 12 and, (6) a mounting plate 44 which mounts the holder 34 to the treatment table (not shown). The transrectal ultrasound probe 12 is mounted in the probe holder 34.

The design for the couch mount 32 has four degrees of freedom for the position of the probe 12 relative to the treatment table, and the standard radiation therapy treatment table has three degrees of freedom for the position of the couch mount 32 relative to the isocenter. The hardware specific geometry is displayed in FIG. 9. The four degrees of freedom for the couch mount 32 are referred to as l, h, Φ, Θ, while the degrees of freedom for the table are referred to as $t_{height}$, $t_{long}$, and $t_{lat}$.

Due to the mathematical nature of the localization algorithm, three points on the ultrasound image must be localized relative to the coordinate origin (isocenter). These three points are arbitrary, insofar as the points must not be collinear, but rather they must define the imaging plane. These three points are referred to as $a^{(1)}$, $a^{(2)}$, and $a^{(3)}$. These three points are exactly determined by the specific values of l, h, Φ, Θ, $t_{height}$, $t_{long}$, and $t_{lat}$. The mode of the ultrasound imaging system also effects these three points since the pixel size of the image is adjustable. This variability is incorporated in the invention, however for the sake of simplicity, only one acquisition mode will be assumed.

The positional information of the probe 12 in the four degrees of freedom are conveyed to the image localization software by any of four methods: manual readouts and key-in, digital readouts and manual key-in, digital encoding and automatic unit entry, and 3D ultrasound or optical ranging (triangulation) with automatic reading of spatial position with respect to the isocenter. With the latter scheme, 3D frameless system replaces the requirement for readouts for each degree of freedom of the probe 12 permitting greater positioning freedom and automatic movement compensation.

The above design enables quantifying the ultrasound imaging plane relative to the isocenter. However, it is also necessary to quantify the radiation field relative to the isocenter. Choosing the coordinate origin as the isocenter, any point in three dimensional space can be deemed and is described by the vector $\vec{r}$. The radiation field is defined by the variables $\Theta_G$, $\Theta_T$, $\Theta_C$, and SAD, where $\Theta_G$ is the gantry angle, $\Theta_T$ is the couch mount 32 or table angle, $\Theta_C$ is the collimator angle, and SAD is the distance from the radiation source to the isocenter. In addition, the field is further quantified by specifying the width and height, given by the symbols w and h. Given these definitions, the points which lie within the radiation field are given by:

$$-w \cdot (SAD-z''')/2SAD \leq x''' \leq w(SAD-z''')/2SAD \quad (3)$$

$$-w \cdot (SAD-z''')/2SAD \leq y''' \leq h(SAD-z''')/2SAD \quad (4)$$

where, $$\begin{pmatrix} x' \\ y' \\ z' \end{pmatrix} = \begin{pmatrix} \cos\Theta_C & \sin\Theta_C & 0 \\ -\sin\Theta_C & \cos\Theta_C & 0 \\ 0 & 0 & 1 \end{pmatrix} \begin{pmatrix} x \\ y \\ z \end{pmatrix} = \begin{pmatrix} x\cos\Theta_C + y\sin\Theta_C \\ -x\cos\Theta_C + y\cos\Theta_C \\ Z \end{pmatrix} \quad (5)$$

$$\begin{pmatrix} x'' \\ y'' \\ z'' \end{pmatrix} = \begin{pmatrix} \cos\Theta_G & 0 & \sin\Theta_G \\ 0 & 1 & 0 \\ -\sin\Theta_G & 0 & \cos\Theta_G \end{pmatrix} \begin{pmatrix} x' \\ y' \\ z' \end{pmatrix} = \begin{pmatrix} x'\cos\Theta_G + z'\sin\Theta_G \\ y' \\ -x'\sin\Theta_G + z'\cos\Theta_G \end{pmatrix}$$

$$\begin{pmatrix} x''' \\ y''' \\ z''' \end{pmatrix} = \begin{pmatrix} \cos\Theta_T & \sin\Theta_T & 0 \\ -\sin\Theta_T & \cos\Theta_T & 0 \\ 0 & 0 & 1 \end{pmatrix} \begin{pmatrix} x'' \\ y'' \\ z'' \end{pmatrix} = \begin{pmatrix} x''\cos\Theta_T + y''\sin\Theta_T \\ -x''\sin\Theta_T + y''\cos\Theta_T \\ Z'' \end{pmatrix}$$

The radiation field can also be defined by the lines which go through the source point and any point on the field edge in the isocentric plane. The field edge can be mapped to the ultrasound imaging plane by determining the intersection of these lines with the plane of the ultrasound image. If the line is described by the two points $\vec{r_1}$ and $\vec{r_1'}$, and the ultrasound imaging plane is described by the above defined points a(i), then the point where this line intersects the imaging plane is given by:

$$t=(D-A \cdot x_1-B \cdot y_1-C \cdot z_1)/A \cdot 1+B \cdot m+C \cdot n) \quad (6)$$

where $$A=(y_2-y_1)(z_3-z_1)-(z_2-z_1)(y_3-y_1) \quad (7)$$

$$B=(z_2-z_1)(x_3-x_1)-(x_2-x_1)(z_3-z_1) \quad (8)$$

$$C=(x_2-x_1)(y_3-y_1)-(y_2-y_1)(x_3-x_1) \quad (9)$$

$$D=A \cdot x_1+B \cdot y_1+C \cdot z_1 \quad (10)$$

and $$l=(x_2-x_1)/d \quad (11)$$

$$m=(y_2-y_1)/d \quad (12)$$

$$n=(z_2-z_1)/d \quad (13)$$

$$d = \sqrt{(x_2-x_1)^2+(y_2-y_1)^2+(z_2-z_1)^2} \quad (14)$$

where t represents the parametric form of a line in three dimensions. The point of intersection is given by $$x=x_1+l \cdot t \quad (15)$$

$$y=y_1+m \cdot t \quad (16)$$

$$z=z_1+n \cdot t \quad (17)$$

With these definitions, the cross sectional field outline as defined in the plane of the ultrasound image can be determined and graphically displayed on the real-time ultrasound image. These coordinates are obtained from the couch mount 32, whereby the method of measurement of the coordinates are obtained by other manual or automatic means consisting of linear and angular vernier position readouts, digitally-encoded readouts, digitally-encoded data to computer, or automatic digital ultrasound triangulation of the four ultrasound probe coordinates. The ultrasound imaging system 10 is directly connected to the PC 50 (see FIG. 2, for example) running the computer software of Appendix A, so that the resultant displayed ultrasound image is in real time.

While particular preferred embodiments of the invention have been shown and described, it will be obvious to those of skill in the art that changes and modifications can be made without departing from the spirit and scope of the invention as set forth in the claims.

What is claimed is:

1. A method of spatially localizing an internal organ of a patient for planning of radiation therapy treatment, comprising the steps of:

(a) producing an ultrasound image by an ultrasound device including at least two fiducials to establish spatial point positions relative to the organ;

(b) generating an additional image of anatomical features proximate to the organ, said additional image generated by another imaging device using means different from ultrasound with said another imaging device including said at least two fiducials from said ultrasound device; and (c) positioning said ultrasound image relative to said additional image, utilizing said at least two fiducials common to each of said images, to form a combined resulting image enabling the radiation therapy to be implemented.

2. The method as defined in claim 1 wherein said ultrasound image is formed by said ultrasound device having end points of an array of transducer elements.

3. The method as defined in claim 2 wherein said array of transducer elements comprises an arc of transducer elements.

4. The method as defined in claim 3 wherein the organ is a prostate gland and said ultrasound probe comprises a transrectal probe.

5. The method as defined in claim 1 wherein said step (c) includes creating a digital map of pixels characteristic of the resulting image, thereby enabling precise localization of said at least two fiducials and associated location of the organ.

6. The method as defined in claim 1 wherein said step (c) comprises a two-dimensional rotation, translation and global isotropic scaling.

7. The method as defined in claim 6 wherein pixel data from said ultrasound image is mapped to pixel data from said additional image.

8. The method as defined in claim 6 wherein only pixel data from said ultrasound image undergoes positioning.

9. The method as defined in claim 6 wherein said step (c) comprises performing a Hough transform.

10. The method as defined in claim 9 wherein said ultrasound image is formed by an ultrasound probe having an outline and said outline is used as a template for the Hough transform.

11. The method as defined in claim 1 further including the step of manually contouring selected anatomical features of the patient.

12. The method as defined in claim 11 wherein the step of manually contouring comprises color washing the selected anatomical features.

13. The method defined in claim 1 wherein each of said ultrasound image, said additional image and said combined resulting image can be displayed by a clinical user for analysis.

14. The method as defined in claim 1 further including the step of superimposing a radiation treatment field portal on said combined resulting image.

15. The method as defined in claim 14 further including the step of preparing a radiation treatment protocol utilizing at least one of said treatment field portal and said resulting image.

16. An apparatus for preparing a patient for radiation therapy of an organ, comprising:
  means for generating an ultrasound image of the organ prior to radiation therapy;
  at least two fiducial elements disposed within the patient to provide spatial point locations relative to the organ, said at least two fiducials being imaged in the ultrasound image;
  means for generating an additional image of anatomical features proximate to the organ, said means for generating an additional image also imaging said at least two fiducials; and
  means for positioning said ultrasound image relative to said additional image of anatomical features, utilizing said at least two fiducials common to each of said images, to form a combined resulting image for assisting in performing the radiation therapy.

17. The apparatus as defined in claim 16 wherein said means for generating an ultrasound image comprises a transrectal ultrasound probe.

18. The apparatus as defined in claim 16 wherein said means for positioning comprises a computer executing computer software.

19. The apparatus as defined in claim 16 wherein said means for generating an additional image comprises at least one of an X-ray unit an MRI unit and a CT unit.

20. An apparatus for monitoring in real time a patient during radiation therapy of an organ, comprising:
  means for adjusting generating an ultrasound image of the organ at least one of prior to and during radiation therapy, said means for generating an ultrasound image including at least two associated fiducials to establish spatial point locations;
  means for generating an additional image of anatomical features proximate to the organ, said means for generating an additional image arising from a different imaging device and imaging said at least two associated fiducials;
  means for juxtaposing said ultrasound image to said additional image of anatomical features, utilizing said at least two fiducials common to each of said images, to form a combined resulting image;
  means for transforming said ultrasound image and localizing said ultrasound image relative to a radiation field isocenter; and
  means for adjusting said radiation field isocenter to maintain the ultrasound image and radiation field isocenter at the same relative location.

21. The apparatus as defined in claim 20 wherein said means for generating an ultrasound image comprises a transrectal ultrasound probe.

22. The apparatus as defined in claim 20 wherein said means for generating an additional image of anatomical features comprises at least one of an X-ray unit and a CT unit.

23. The apparatus as defined in claims 20 wherein said means for transforming comprises a computer executing computer software.

* * * * *

UNITED STATES PATENT AND TRADEMARK OFFICE
CERTIFICATE OF CORRECTION

PATENT NO. : 5,810,007
DATED : September 22, 1998
INVENTOR(S) : Holupka et al.

It is certified that error appears in the above-identified patent and that said Letters Patent is hereby corrected as shown below:

In Column 1, line 49, delete "defme" and insert --define--.
In Column 3, line 17, delete "object" and insert --objects--.
In Column 4, line 24, before "computer", insert --conventional--.
In Column 4, line 25, delete "(to be described hereinafter and/or set forth in Appendix A)".
In Column 4, line 40, delete "$r_{is}$" and insert "$r_{si}$".
In Column 5, line 51, delete "appear" and insert --appears--.
In Column 5, line 66, delete "(see attached Appendix A)" and insert --described hereinbefore in relation to the conventional mathematical transformation of Equations (1) and (2)--.
In Column 7, line 14, delete "defme" and insert --define--.
In Column 8, line 8, insert a left parenthesis "(" before "$A \cdot l + B \cdot m + C \cdot n$)".
In Column 8, line 47, delete "of Appendix A".
In Column 10, line 19, insert a comma "," after "X-ray unit".
In Column 10, line 22, delete "adjusting".

Signed and Sealed this

Eleventh Day of May, 1999

Attest:

Attesting Officer

Q. TODD DICKINSON

Acting Commissioner of Patents and Trademarks